US00PP35410P3

(12) United States Plant Patent
Bouchet

(10) Patent No.: US PP35,410 P3
(45) Date of Patent: Oct. 3, 2023

(54) WHITE PEACH TREE NAMED 'SWEETJAZZY'

(50) Latin Name: ***Prunus persica* (L.) *Batsch.***
Varietal Denomination: SWEETJAZZY

(71) Applicant: AGRO SELECTIONS FRUITS, Elne (FR)

(72) Inventor: Christophe Bouchet, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 18/070,668

(22) Filed: Nov. 29, 2022

(65) Prior Publication Data

US 2023/0172086 P1 Jun. 1, 2023

(30) Foreign Application Priority Data

Nov. 30, 2021 (QZ) ..... PBR 2021/3100

(51) Int. Cl.
*A01H 5/08* (2018.01)
*A01H 6/74* (2018.01)

(52) U.S. Cl.
USPC ..... Plt./195
CPC ..... *A01H 6/7463* (2018.05)

(58) Field of Classification Search
USPC ..... Plt./195
CPC ..... A01H 6/7463; A01H 5/08
See application file for complete search history.

*Primary Examiner* — Keith O. Robinson
(74) *Attorney, Agent, or Firm* — Birch, Stewart, Kolasch & Birch, LLP

(57) ABSTRACT

A new and distinct variety of white peach tree denominated 'SWEETJAZZY' which has fruits with high eating quality and very long shelf life without alteration before and after harvesting, with a semi-sweet white flesh at maturity time, having a slightly pink pigmentation around the stone cavity, and an attractive skin with a luminous purple red blush on skin surface, on a purple red background.

5 Drawing Sheets

Botanical classification: *Prunus persica* (L.) Batsch.

Variety denomination: 'SWEETJAZZY'.

This application claims priority of Community Plant Variety Right No. 2021/3100 filed on Nov. 30, 2021 which is hereby incorporated by reference in its entirety.

The new variety named 'SWEETJAZZY' is also known as 07.06.400.17 PB or ASF2004. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'SWEETJAZZY', the provisional reference of this white peach tree variety was 07.06.400.17, corresponding to the tree 400 located in line 06 of the parcel 07 and selected during the year 2017. The letters "PB" are related to the first letters of the type of tree in French (PB for "Pêche Blanche", that means "white peach"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'SWEETJAZZY', the clone reference was 'ASF2004'.

BACKGROUND OF THE NEW VARIETY

The present invention relates to a new and distinct variety of white peach tree, *Prunus persica* (L.) Batsch, which has been given the variety denomination 'SWEETJAZZY'.

This new tree produces fruits with a long shelf life without alteration both on the tree after growth completion and after harvesting, very good eating quality, semi-clingstone white and slightly pinkish flesh fruits at maturity, with no pigmentation around and into the stone cavity, for fresh market during June in the Pyrénées-Orientales department, France.

ORIGIN OF THE VARIETY

The 'SWEETJAZZY' white peach tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year and are mostly found in Spring and Autumn. In May and October, very intense precipitations occasionally happen. Summer is dry with a few thunderstorms.

The 'SWEETJAZZY' variety results from a controlled pollinated cross between the yellow peach variety named 'CRISPTOLAM' (not patented) which was used as the seed parent, or female parent, and the white peach variety named 'SWEETALY' (not patented) which was used as the pollen parent, or male parent.

The 'SWEETJAZZY' variety was obtained by hybridizing and propagated by grafting on a 'INRA® GF677' (non-patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree, and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'SWEETJAZZY' white peach tree blooms mid-February near Elne in the Pyrénées-Orientales department, France. The blooming period is considered early. However, it was observed that its date of blooming seems to be highly dependant on climatic conditions.

The first fruit of 'SWEETJAZZY' ripens generally early in the season, namely first week to mid-June. However, it was observed that its date of maturity seems to be highly dependant on climatic conditions.

DESCRIPTION OF THE DRAWINGS

In the accompanying drawing, which are as nearly true as it is reasonably possible to make in a color illustration of this type.

Figure 1:
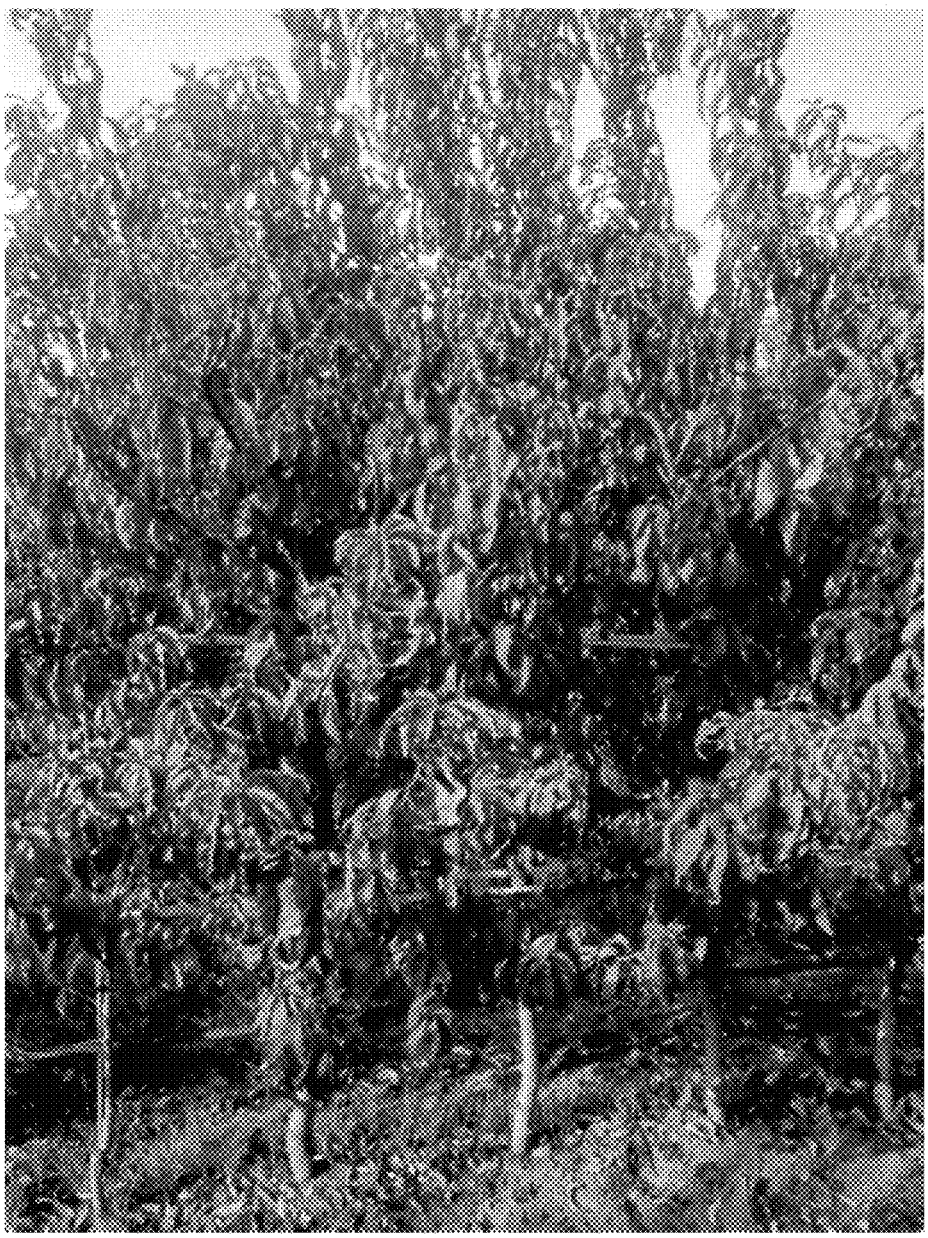
FIG. 1 is a color photograph showing trees of the new variety 'SWEETJAZZY' in orchard.
Figure 2:
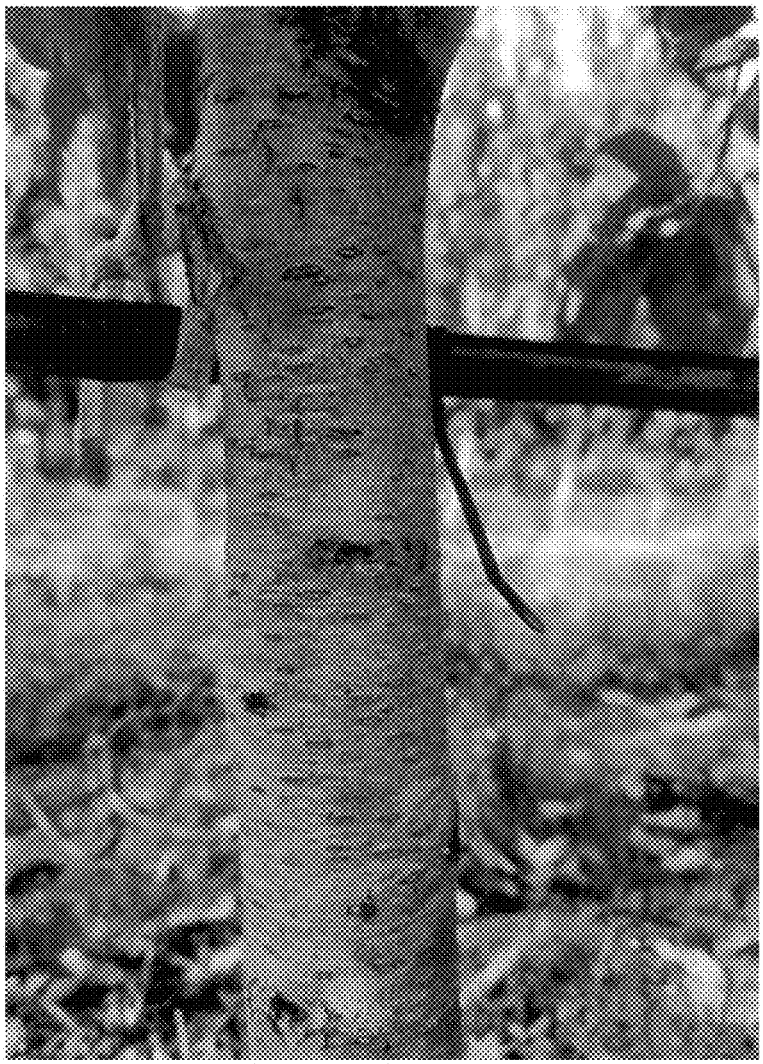
FIG. 2 is a color photograph showing a close view of the trunk of a tree in orchard.
Figure 3:
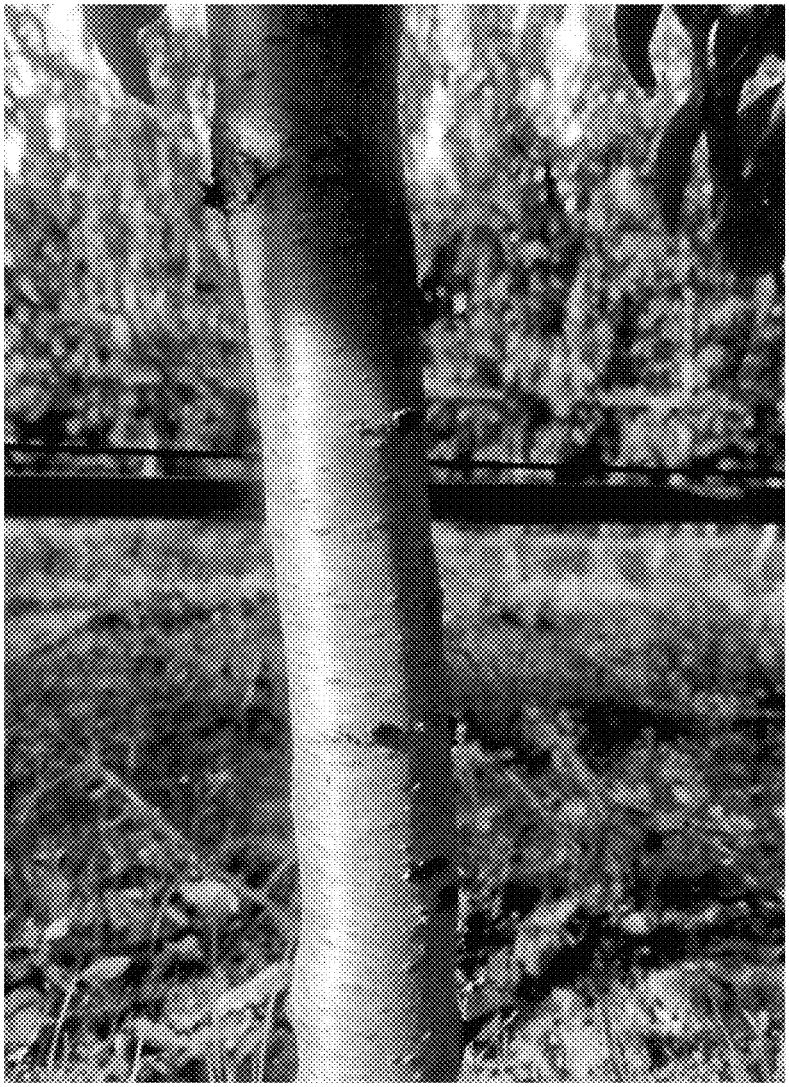
FIG. 3 is also a color photograph showing a close view of the trunk of a tree in orchard.
Figure 4:
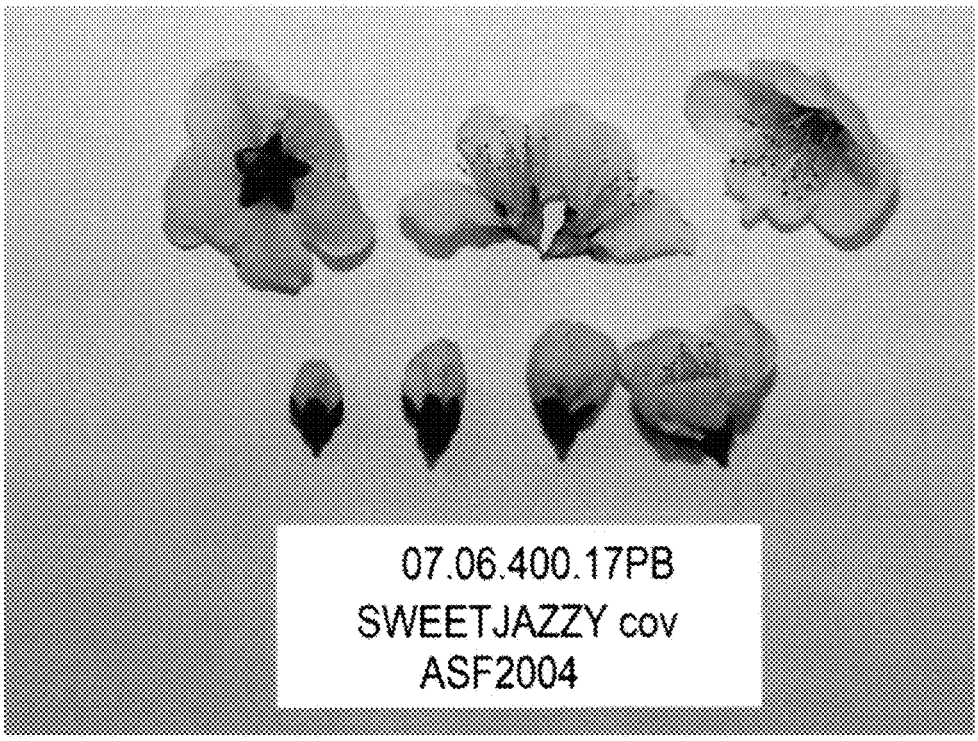
FIG. 4 is a color photograph which depicts the flower buds at different development stages, and the reverse and side views of the flower and the reproductive organs with petals removed, of the new variety 'SWEETJAZZY' also named '07.06.400.17 PB-ASF2004'.
Figure 5:
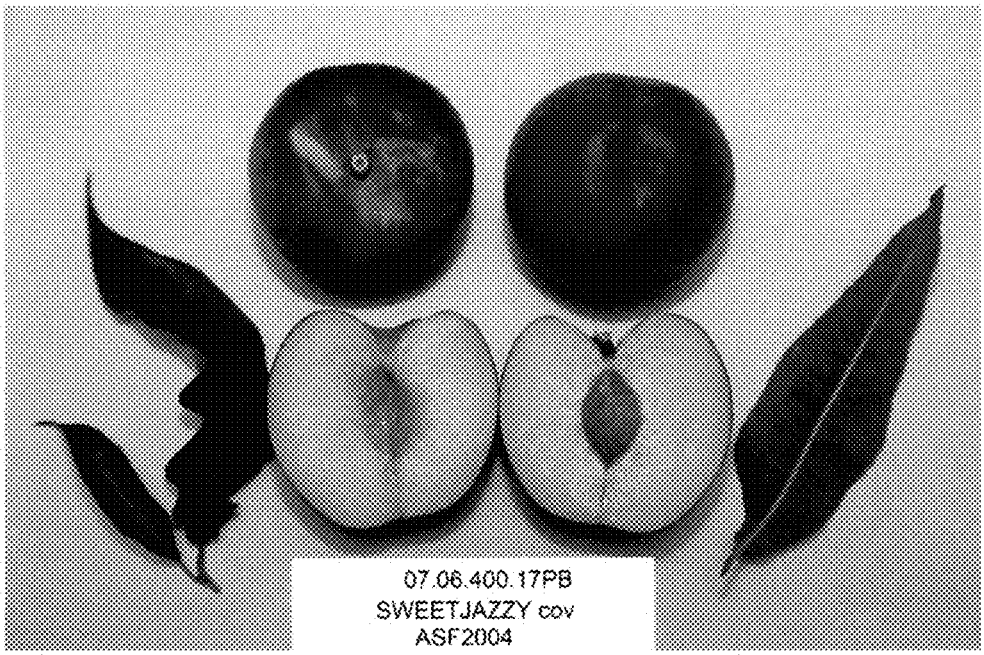
FIG. 5 is a color photograph which shows the upper and lower sides of leaves and different views of three typical specimens of the fruit of the new variety 'SWEETJAZZY' also named '07.06.400.17 PB-ASF2004' at ripening time, one fruit having been cut in half with the pit being left in one of the halves for depicting leaves, fruit flesh, pit and pit cavity of the new variety.
Figure 6:
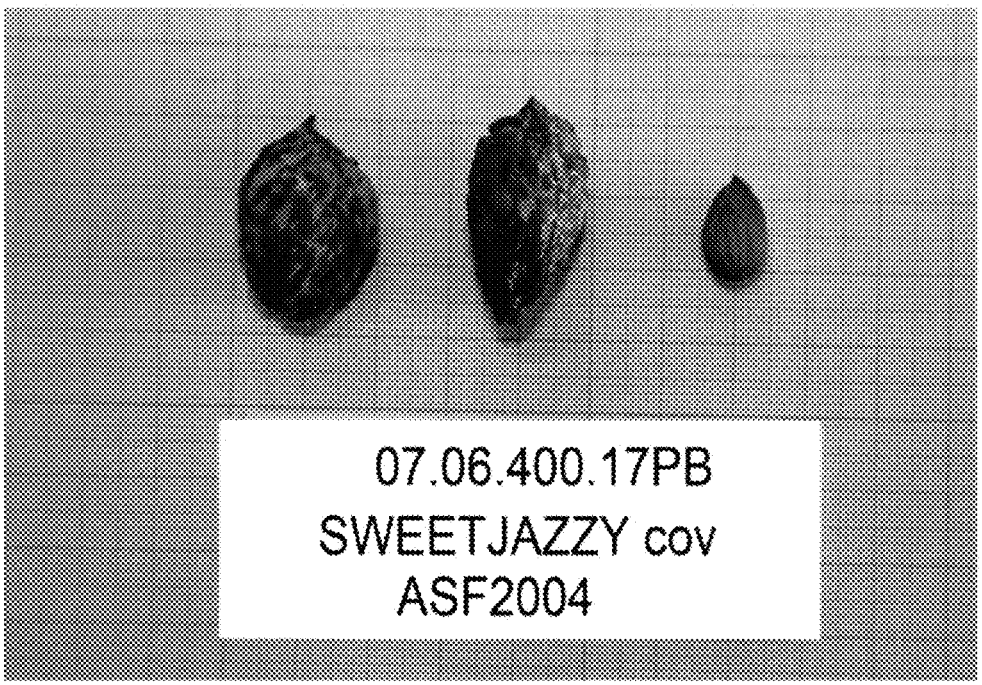
FIG. 6 is a color photograph showing different views of the stone of the new variety 'SWEETJAZZY' also named '07.06.400.17 PB-ASF2004' and the kernel of the stone.

The views of trees, flowers, leaves and fruits have been photographed in their third growing season (second year of production).

Due to chemical development, processing and printing, the flowers, stones and fruits depicted in these photographs may or may not be accurate when compared to the actual botanical specimen.

DETAILED BOTANICAL DESCRIPTION

The trees, flowers, and fruits may vary in slight detail due to variations in soil type, cultural practices, and climatic condition. The potential for commercial production of fresh fruits by 'SWEETJAZZY' is high, due to fruit very long shelf life without alteration after harvesting.

Trees are medium to strong vigorous and large stature half-standing in a semi-flared out aspect. The anthocyanic coloration of flowering shoot is present excluding brushwood side away from sun. The time of beginning of flowering is considered early; flowering starts mid-February. The type of flower is showy (rosette) with small to medium petal size. Petals are pink. Leaf glands are present and reniform. The fruit flesh is white and may usually shows a slightly pinkish pigmentation around the stone cavity. The fruit skin is medium thick, with a luminous purple red blush on a purple red background. The new variety 'SWEETJAZZY' presents fruits having a good presentation with a nice round shape and a good firmness, with a white flesh having a slightly pinkish pigmentation and a good taste for the early maturity time. The stone is semi-clingstone and its size is small. Fruit taste is semi-sweet, and medium aromatic.

Compared to the white peach variety named 'SWEETPRIM' (U.S. Plant Pat. No. 21,157) the fruits of 'SWEETJAZZY' usually ripen approximately during the same period. The flowering period of the new variety 'SWEETJAZZY' is slightly earlier than the flowering period of the similar variety named 'SWEETPRIM'. The flavor of the flesh of the new variety 'SWEETJAZZY' is considered semi-sweet whereas the flavor of the similar variety 'SWEETPRIM' is semi-sweet to balanced.

Compared to its seed or female parent, i.e., the 'CRISPTOLAM' (not patented) variety, the new variety 'SWEETJAZZY' has not the same flesh color. The flesh color of the 'CRISPTOLAM' fruits is considered yellow, whereas the flesh color of the new variety fruits is considered white with a slightly pink pigmentation radiating around the stone cavity.

Compared to its pollen parent 'SWEETALY' white peach tree (not patented), the new variety 'SWEETJAZZY' ripens two weeks later.

DETAILED DESCRIPTION

Referring more specifically to the pomological details of this new and distinct variety of white peach tree, the following was observed on trees in their third growing season (second year of production) under the ecological conditions prevailing at the orchards located near the town of Elne, Pyrénées-Orientales departement, France. All observations have been done on rootstock cultivars. Used rootstocks were 'INRA® GF677' (non-patented) trees. All major color code designations are by reference to The R.H.S. Colour Chart (Fourth Edition) provided by The Royal Horticultural Society of Great Britain.

Tree:

*Size*.—Generally. — Considered large. The tree size the first year was approximately 200 to 280 cm in height. The tree was pruned during each following dormant season to a height of approximately 250 cm. Current season shoots growth could reach 80 cm in length. The tree size from the second year (second and next years) reached a final height of 330 cm including current season shoots length. The tree size is consistently reduced to 250 cm the next years.

*Spread*.—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor*.—Considered medium to strong.

*Productivity*.—Considered good to very good and regular. Fruit set is spaced by thinning to develop the remaining fruit into the desired market sized fruit. The number of the fruit set varies with the prevailing climatic conditions and cultural practices employed during the bloom period and is therefore not distinctive of the present variety. A reduce vegetation, obtained with pruning or green pruning, approximately 1 month or 1 month ½ before harvesting fruits, significantly promotes fruit qualities, especially growth, color and firmness. Moreover, contamination risks due to monilia or rot are significantly reduced. 'SWEETJAZZY' variety is not much sensitive to cracking of pistil cavity, to cork formation into peduncle cavity or to monilia.

*Bearer*.—Very regular. The fruit distribution is considered homogenous on mixed branches and spurs having more than 1 year. Thinning of 2 fruits out of 3 was necessary for the tree valorisation. Thinning was necessary every year during the years of observation.

*Form*.—The 'SWEETJAZZY' variety has naturally a semi-flared shape.

*Density*.—Considered dense.

*Hardiness*.—Hardy in all stone fruit growing areas of France and especially where the chilling requirement is between 700 and 1200 hours. More particularly, experimentations on the same orchard in Elne, Pyrénées-Orientales department, with winter chilling requirement below 7.2° C. comprised between 700 hours and 1200 hours according to the specificities of the year, namely 1031 hours in 2012-2013, 777 hours in 2013-2014, 893 hours in 2014-2015, 718 hours in 2015-2016, 825 hours in 2016-2017,1017 hours in 2017-2018, 844 hours in 2018-2019, 706 hours in 2019-2020, 822 hours in 2020-2021 and 700 hours in 2021-2022 showed a good behavior of the tree in all cases. No injury with temperatures as low as −12° C. in winter. Good resistance to late frosts.

Trunk:

*Diameter*.—Approximately 43.0 to 49.0 millimeters in diameter when measured at a distance of approximately 20.0 centimeters above the soil level for trees on fourth leaf (or third year of production).

*Bark texture*.—Considered rough, with lenticels.

*Lenticels*.—Lenticels are present. The number of lenticels reaches 2 lenticels per $cm^2$. The lenticels range in size of approximately 4.0 to 5.0 millimeters in width, and about 1.5 to 2.0 millimeters in height.

*Lenticel color*.—The lenticels show a beige color (RHS Greyed Orange 164 B).

*Bark coloration*.—The bark has a brown to grey color (RHS Brown 199 B) darker than the lenticels color.

Branches:

*Size*.—The branches are pruned to approximately 1.0 meter in length.

*Diameter*.—Average as compared to other peach varieties. The current season shoots have a diameter of approximately 4.0 to 6.0 millimeters, and mature branches (two year's old branches) have a diameter of approximately 10.0 to 14.0 millimeters.

*Surface texture*.—Smooth for current season shoots and rough, with lenticels, for mature branches, wood which is several years old has furrowed appearance.

*Crotch angles*.—Primary branches are considered variable, but the crotch angles are generally 45 degrees from the horizontal axis for current season shoots and 55° degrees from the horizontal axis for two year's old branches. This particular characteristic is not considered distinctive of the variety, however.

*Current season shoots*.—

*Internode length*.—Generally 16.0 to 19.0 millimeters. Color. — The color of new shoot tips is considered green (RHS Yellow Green 145 A) on lower part of new shoot tips, whereas the upper part is darker and colored in brown to purple (RHS Greyed Red 183 A), depending on the level on the tip and the sunlight exposure.

*Mature branches*.—

*Internode length*.—Generally between 24.0 and 28.0 millimeters.

*Color of mature branches*.—Brown (RHS Grey Brown 199 A or RHS Grey Brown N 199C).

*Lenticels*.—Numerous lenticels are present on mature branches. The number of lenticels reaches 3 lenticels per $cm^2$. The size of lenticels is considered small on one year's old shoots and medium on two-year-old shoots. The lenticel shape is round with a diameter of approximately 1.0 to 1.5 millimeter on one-year-old shoots. The lenticel shape is stretched round with a diameter of 1.5 to 2.0 millimeters on two-year-old shoots.

*Lenticel color*.—The lenticels on mature branches have a beige color (RHS Greyed Orange 164 A or RHS Greyed Orange 164 B).

Leaves:

*Size*.—Considered medium to large for the species. The ratio leaf length/leaf width is 3.556.

*Leaf length*.—The medium length is about 152.0 millimeters with leaf petiole.

*Leaf width*.—The medium width is 42.75 millimeters.

*Leaf form* (*in cross section*): Concave.

*Leaf form*.—Lanceolate.

*Leaf base shape*.—Round.

*Leaf tip form*.—Acute.

*Leaf thickness*.—Medium.

*Leaf color*.—Upper leaf surface. — Yellow Green (RHS Yellow Green 147 A). Lower surface/ — A slightly lighter green (RHS Yellow Green 146 A) than the upper leaf surface color.

*Leaf texture*.—Smooth and glabrous on both upper and lower surfaces of the leaf.

*Leaf venation*.—Pinnately veined.

*Mid-vein*.—Color. — Light green (RHS Yellow Green 145 B to RHS Yellow Green 145C). The color may evolve with maturity. Width. — Approximately 1.0 millimeters.

*Secondary veins*.—Color. — Light green (RHS Yellow Green 144 B).

*Leaf margins*.—Slightly undulating.

*Form*.—Considered crenate.

*Uniformity*.—Leaves are isolated or grouped by 2 or 3. In this last case, one leaf of normal size is found with one or two smaller leaves (at least 50% smaller).

*Leaf petioles*.—Size. — Considered small to medium. Length. — About 8.0 to about 10.0 millimeters. Diameter. — About 2.0 millimeters. Shape. — Grooved.

*Petiole color*.—Upper petiole surface. — Green (RHS Yellow Green 145 A). Lower surface. — A slightly lighter green (RHS Yellow Green 145 B) than the upper petiole surface color. Ratio leaf length/petiole length. — Approximately 17.

*Leaf glands*.—Size. — Considered medium. Their length is about 1.2 millimeter and their width is about 1.0 millimeter. Number. — Generally 2 glands per leaf. Type. — Reniform. Margins. — Smooth and regular. Position. — Alternate on the upper part of petiole. Color. — On young leaves, leaf glands color is considered a light green (RHS Yellow Green 145 B). On older leaves, leaf glands color turns to a brown (RHS Brown 200 B) color.

*Leaf stipules*.—Generally. — No leaf stipules were observed. But as seen in the characteristic relative to the leaves uniformity, it is possible to find leaves by groups of 2 or 3, with a normal-size leaf and smaller ones.

Flowers:

*Flower buds*.—Generally. — At pre-floral stage of development, the floral buds are round in shape. Their form is evolving until blooming, with variable dimensions. Just before blooming, floral buds are approximately 8.0 to 10.0 millimeters wide and approximately 13.0 to 19.0 millimeters long. The floral buds show a homogenous distribution on the trees. Color. — This characteristic is dependent upon the proximity to bloom. At pre-floral stage of development, the bottom of the flower's buds, or calyx, or flower receptacle, is of purple color (RHS Greyed Purple 187 A to RHS Greyed Purple 187 B) on its outer face. The inner face of the flower receptacle is orange yellow (RHS Yellow Orange 23 B). The corolla, formed by the petals, is generally of pink color (RHS Red Purple 62 B) on both faces. Petals color shows an evolution until the end of flowering.

*Hardiness*.—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom*.—The blooming time generally begins mid-February. The first bloom was observed on Feb. 2, 2020.

*Blooming time*.—Considered early in relative comparison to other commercial peach cultivars grown in the Pyrénées-Orientales departement, France. The date of full bloom is observed generally at the middle of the blooming period. The date of bloom varies slightly with climatic conditions and cultural practices. Thus, the full bloom was observed in 2020, from February 2$^{nd}$ until February 14$^{th}$, then from February 15$^{th}$ to February 26$^{th}$ in 2021 and then from February 8$^{th}$ to Feb. 17, 2022.

*Duration of bloom*.—Medium, approximately between 8 to 10 days. This characteristic varies slightly with the prevailing climatic conditions.

*Flower type*.—The variety is considered to have a showy type of flower.

*Flower size*.—Considered medium. Flower diameter at full bloom is approximately 33.0 to 35.0 millimeters.

*Bloom quantity*.—Considered high, approximately 50 to 60 flowers per meter, with a high rate of fruit set.

*Flower bud frequency*.—Generally 2 flower buds appear per node, occasionally 1.

*Petal size*.—Generally. — Considered small to medium.

*Length*.—Generally between 15.0 and 16.0 millimeters.

*Width*.—Generally between 14.0 and 15.0 millimeters.

*Petal form*.—Round-shaped.

*Petal count*.—Usually five.

*Petal arrangement*.—Overlapping.

*Petal texture*.—Smooth on both upper and lower surfaces of the petal.

*Petal color*.—At the stage F of blooming, when the flower is fully opened, both surfaces of the petal are colored with a pink (RHS Red Purple 62 B) color when young, becoming slightly darker until the end of blooming.

*Fragrance*.—Light to moderate floral fragrance.

*Petal claw*.—Form. — The claw is considered to have a narrow form. Length. — About 1.25 to 1.5 millimeters. Width. — About 1.5 millimeters at the base. Color. — The petal claw usually shows a pink color darker than the petal color (RHS Red Purple 59 C).

*Petal margins*.—Generally considered slightly undulating.

*Petal apex*.—Generally. — The petal apices are generally shaped as a wide dome.

*Flower pedicel*.—Length. — Considered medium and having an average length of approximately 3.0 to 4.0 millimeters. Diameter. — Considered average, approximately 1.0 to 1.5 millimeters. Color. — Green (RHS Yellow Green 144 A).

*Calyx*.—Internal surface texture. — Smooth. Color. — At the stage F of blooming, when the flower is opened, the inner surface of the calyx, namely the flower receptacle, is yellow orange to slightly greenish (RHS Yellow Orange 23 A). The outer surface of the calyx is considered of purple color (RHS Greyed Purple 187 A or RHS Greyed Purple 187 B).

*Sepals*.—

*Sepal count*.—Usually 5 sepals. Surface texture. — The outer surface has a short, fine pubescent texture. Margins. — smooth. Size. — Medium. Length. — Approximately 4.0 to 5.0 millimeters. Width. — Approximately 4.0 to 5.0 millimeters. Form. — Conic and round at the top. Color. — The upper surface of the sepals shows a purple color (RHS Greyed Purple 187 A or RHS Greyed Purple 187 B) whereas the lower surface of sepals is considered greenish (RHS Yellow Green 152 A).

*Anthers*.—Generally. — Medium in length, approximately 1.0 millimeter. Shape. — Cordate Color. —

Depending on the maturity stage, anthers are colored with a red (RHS Red 53 A) to a yellow color (RHS Yellow Orange 20 A).

*Pollen production*.—Pollen is abundant and has a yellow color (RHS Yellow 11 A) which may evolve with maturity. The present variety is considered auto-fertile (self-pollinating).

*Pistil*.—Number. — Usually 1. Generally. — Average in size. Length. — Approximately 12.0 to 14.0 millimeters including the ovary. Generally equal to or higher than filaments in length when considered without the ovary. Color. — Considered green to yellow (RHS Yellow Green 150 C or RHS Red Purple 62 C) at the beginning of blooming period. Position. — The pistil is positioned below the stamens, or at the same level.

*Ovary*.—Height. — Approximately 1.5 to 2.0 millimeters. Diameter. — Approximately 1.5 to 2.0 millimeters. Color. — Green (RHS Yellow Green 145 A). Pubescence. — The ovary is pubescent.

*Stamens*.—Size compared to petals. — The size of stamen is smaller than the size of petals. Length. — Approximately 11.0 to 13.0 millimeters, usually equal to or smaller than the pistil length (considered without the ovary). Color. — White (RHS White N 155 B) to pink (RHS Red Purple 62 C) depending on the maturity stage.

*Average number of stamens per flower*.—Approximately 27 to 34 stamens per flower.

*Stigma*.—Diameter. — Approximately 1.0 millimeter. Color. — Greenish yellow (RHS yellow Green 151 D). Shape. — Round. Position of the stigma compared to the anthers. — The stigma is above the anthers.

Fruit:

*Maturity when described*.—Firm in ripe conditions (shipping ripe).

*Date of first picking*.—Jun. 25, 2019.

*Date of last picking*.—The date of harvest varies slightly with the prevailing climatic conditions. The 'SWEETJAZZY' variety has a very early to early date of picking, and a grouped maturity. The maturity is grouped within 6 to 9 days and the harvest is generally performed in two runs. Picking times carry on from June 25$^{th}$ to Jun. 30, 2019, then from June 5$^{th}$ to Jun. 13, 2020, then from June 16$^{th}$, to Jun. 24, 2021 and then from May 30$^{th}$, to Jun. 7, 2022.

*Size*.—Generally. — Homogeneous in size, size A or B or C. Considered medium.

*Average cheek diameter*.—Approximately 69.0 to 71.0 millimeters.

*Average axial diameter*.—Approximately 63.0 to 67.0 millimeters.

*Typical weight*.—Approximately 158.40 grams. This characteristic is high dependent upon the prevailing cultural practices, and therefore is not particularly distinctive of the variety.

*Fruit form*.—Generally. — Very round, regular and symmetrical. The fruit is generally uniform in symmetry, viewed from the suture's plane.

*Suture*.—

*Fruit suture*.—The suture is usually wide-mouthed and slightly marked when present, located from the base to the apex but more pronounced near the base. No apparent callousing or stitching exists along the suture line. Not pointed.

*Ventral surface*.—Form. — Smooth.

*Apex*.—Slightly depressed. Mucron. — Slightly marked. Closing of the pistil cavity. — Very good. The pistil cavity is not visible.

*Stem cavity*.—Average depth of the stem cavity is considered medium, about 6.0 to 9.0 millimeters. Average width is between 15.0 and 21.0 millimeters, and the stem cavity is flared.

*Fruit skin*.—Thickness. — Considered medium and strong, and the skin adherence to flesh is semi-adherent. Texture. — The pubescence of the skin is thin. Taste. — Semi-sweet. Tendency to crack. — None observed.

*Color*.—Blush color. — This blush color is a uniform luminous purple red (RHS Greyed Purple 187 A). The purple red blush covers approximately 95% of the fruit skin surface on a red background (RHS Greyed Purple 185 A) on approximately 5% of the fruit skin surface. The percentage of the blush on the fruit skin surface can vary and is generally dependent upon the prevailing conditions under which the fruit was grown. Ground color. — The ground color covers approximately 5% of the fruit skin surface, and is considered red (RHS Red 185 A). Lenticels. — No lenticel.

*Fruit stem*.—Medium in length, approximately 6.0 to 7.0 millimeters.

*Diameter*.—Approximately 4.0 to 5.0 millimeters.

*Color*.—Pale green (RHS Yellow Green 145 A).

*Flesh*.—Ripens. — Very homogenously, slowly. The flesh has a long shelf life. Texture. — Firm to very firm, crunchy, melting, at harvest maturity stage. Fibers. — Not fibrous. Aroma. — Medium, semi-sweet, sugary and fruity. Eating quality. — Considered good, semi-sweet. Flavor. — Considered semi-sweet. The Brix is generally superior to 11, with an average value at 12.3, and acidity is low. Juice. — Juicy at complete maturity. The juice shows a cream color (RHS NN155B). Brix. — The medium Brix is 12.3 degrees. This characteristic varies slightly between 11.2 and 13.4 with the number of fruits per tree, prevailing cultural practices and the surrounding climatic conditions. Flesh color. — The flesh is considered white (RHS White 155 A), with a slightly pink pigmentation (RHS Red 47 A) radiating around the stone cavity.

Stone:

*Type*.—Semi-Clingstone, more or less semi-adherent depending on the fruit maturity.

*Size*.—Considered small for the variety. The stone size varies significantly depending upon the tree vigor, crop load and prevailing growing conditions.

*Length*.—Approximately 20.0 to 24.0 millimeters.

*Width*.—Approximately 16.0 millimeters.

*Diameter*.—Approximately 15.0 millimeters.

*Form*.—Elliptical.

*Base*.—Round.

*Apex*.—Shape. — The stone apex is short and pointed.

*Stone cavity*.—Considered small in size, approximately 12.0 to 15.0 millimeters with elliptic form and dimensions corresponding to the stone's dimensions.

*Stone surface*.—Surface texture. — The pit is transversely furrowed on its entire surface. Furrows are deeper and more oblate on lateral sides. Ridges. — The surface texture is generally characterized by more prominent ridges along the ventral edges and at the apical tip.

*Ventral edge*.—Width. — Narrow. Approximately 2.0 millimeters at mid-suture.

*Dorsal edge*.—Shape. — Grooved.

*Stone color*.—The color of the dry stone is generally considered light brown (RHS Greyed Orange 164 B or RHS Greyed Orange 164 C).

*Tendency to split*.—Splitting is absent.

*Kernel*.—Size. — The kernel is considered small. Length. — Approximately 12.0 millimeters. Width. — Approximately 7.0 millimeters. Thickness. — Approximately 5.0 millimeters. Form. — Considered elliptical. Pellicle. — The pellicle of the kernel has a short pubescence. Color. — The kernel skin is light brown colored (RHS Greyed Orange N167 A). The almond, which is the seed of the kernel, is white (RHS White 155 B) and has a sweet taste. The kernel and its embryo are mature at the time of fruit maturity.

*Use*.—The subject variety 'SWEETJAZZY' is considered to be a white peach tree having an early season of maturity, and which produces fruits that are considered firm, attractively colored with a luminous purple red. Fruits have semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long-distance shipping.

*Keeping quality*.—Remarkable. Fruits have a slow maturation and a long shelf life both on the tree after growth completion and after harvesting without alteration. After growth completion, fruits are preserved more than one week. After harvest, fruits are well preserved more than 2 weeks at 2.0 degree Celsius.

*Shipping quality*.—Considered very good. The fruit of the new white peach variety showed minimal bruising of the flesh or skin damage after being subjected to normal harvesting and packing procedures. Its resistance to handling during harvest and packing and its long shelf life without alteration after harvest easily permit 2 weeks-shipping at 2 degrees Celsius.

*Resistance to insects and disease*.—No particular susceptibilities were noted. The present variety is not very sensitive to *Monilia* or rot. The pistil cavity is completely closed, generally without any cork formation.

Although the new variety of white peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of white peach tree named SWEETJAZZY as illustrated and described, characterized by fruits with high eating quality and very long shelf life without alteration before and after harvesting, with a semi-sweet white flesh at maturity time having a slightly pink pigmentation around the stone cavity, and an attractive skin with a luminous purple red blush on skin surface, on a purple red background.

* * * * *